United States Patent [19]

Hollander et al.

[11] Patent Number: 4,652,577

[45] Date of Patent: Mar. 24, 1987

[54] DENATONIUM SACCHARIDE, COMPOSITIONS AND METHOD OF USE

[75] Inventors: Gary T. Hollander, Obetz, Ohio; Mel Blum, Wantagh, N.Y.

[73] Assignee: Atomergic Chemetals Corporation, Plainview, N.Y.

[21] Appl. No.: 667,776

[22] Filed: Nov. 2, 1984

[51] Int. Cl.$^4$ ............................................ C07D 275/06
[52] U.S. Cl. ................................... 514/373; 548/211; 514/920
[58] Field of Search ................. 548/210, 211; 514/373

[56] References Cited

U.S. PATENT DOCUMENTS 2,725,326  11/1955  Shibe et al. ........................ 548/211
4,064,316  12/1977  Curtis et al. ........................... 424/2

FOREIGN PATENT DOCUMENTS 39-1243  2/1984  Japan ................................. 548/211

OTHER PUBLICATIONS (Annon.), "Denatonium Benzoate as Deterrent for Ingestion...," C.A.97:50752(v) (1982).
Bartoshwk, Linda, "Bitter Taste of Saccharin Related to the Genetic Ability..." C.A.91:138135(h) (1979).
Saroli, A., "Structure–Activity Relationship of a Bitter Compound...," C.A.101:169274(g) (1984).

*Primary Examiner*—Glenna M. Hendricks
*Attorney, Agent, or Firm*—Jordan and Hamburg

[57] ABSTRACT

Denatonium saccharide, which has a vile, bitter taste, is applied to protect an article against gnawing, biting, licking, and feeding by various animals.

4 Claims, No Drawings

DENATONIUM SACCHARIDE, COMPOSITIONS AND METHOD OF USE

BACKGROUND OF THE INVENTION AND PRIOR ART STATEMENT

This invention relates to denatonium salts which possess bitter tasting properties, and to compositions and methods of using such compounds as bittering agents. More particularly, it is concerned with the novel compound denatonium saccharide which shows an unusually pronounced bitter tasting effect.

The literature has described the bitter tasting property of denatonium benzoate, and its use as a denaturing substance for alcohol and paint formulations, and as a deterrent in animal compositions; such references include U.S. Pat. Nos. 3,080,326; 3,080,327; 3,268,577; 3,935,137; 4,005,038; and 4,064,316; Ger. Pat. Nos. 2,642,606; 2,942,537 and 2,942,581; Brit. Pat. No. 866,605; and Europat. No. 12,525.

While denatonium benzoate has a marked bitter tasting property, it is desired to provide new and useful compounds which would exhibit an enhanced bitter tasting property, and which can be readily formulated into compositions, and applied into or onto different substrate materials.

Accordingly, it is the object of the present invention to provide a new and improved bitter tasting denatonium compound having a bitter tasting property at very low concentrations.

SUMMARY OF THE INVENTION

In accordance with the object of the invention, there is provided herein the compound denatonium saccharide, which is believed to be the bitterest substance known, being five times more bitter than denatonium benzoate. The denatonium saccharide compound of the present invention exhibits a bittering taste effect even in a dilution ratio of 1:100 million. Due to its unusual property, denatonium saccharide is a material of choice in many practical applications of a bittering agent.

Denatonium saccharide has the following chemical formula:

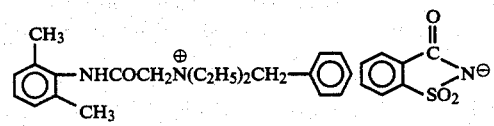

Its chemical name is:

N,N,N,N.Benzyldiethyl [(2,6-xylylcarbamoyl)-methyl] ammonium saccharide.

DETAILED DESCRIPTION OF THE INVENTION

Denatonium saccharide is prepared by heating equivalent amounts of a denatonium halide, e.g. denatonium chloride, with an alkali metal salt of saccharin, e.g. sodium saccharide, in a solvent medium, e.g. water, at an elevated temperature, generally about 55°–65° C. The product is recovered in crystalline form by solvent extraction and precipitation. The starting material denatonium chloride is prepared by reacting the corresponding tertiary amine, lidocaine, with bensyl chloride.

Accordingly, denatonium chloride, 10 g, in 100 ml distilled water at 55°–65° C. was magnetically stirred and 7.94 g solid sodium saccharide was added to give an initially gelatinous oil which solidified on stirring. The solid was taken up in chloroform, the solution reduced to incipient dryness and the resulting oil was heated with 15 ml of isopropanol to give a solution to which was added 100 ml ethyl acetate to give a fine white powder, 11.76 g (80.5% yield) of denatonium saccharide, m. 177°–8° C. soluble in chloroform, isopropanol, dimethyl sulfoxide and slightly soluble in water.

Compositions for utilizing the bitter tasting property of denatonium saccharide at low concentrations include an effective amount of denatonium saccharide, and an inert and/or active material therewith, e.g. organic solvents, such as sodium lauryl sulfate or dimethylsulfoxide useful in formulating denatonium saccharide also may be imparted onto or into a substrate by including an effective amount of denatonium saccharide therewith. This use is particularly effective as animal repellant applications, e.g., in protecting plastic cable sheathing against attack by rodents, where the plastic is impregnated by pellets of denatonium saccharide during the melting of the plastic, and in protecting plants from attack by rodents, deer, birds, cats, dogs, etc. Many of these applications are favored by the essentially non-toxic property of denatonium saccharide, it having an $LD^{50}$ of 1500 mg/kg.

What is claimed is:
1. Denatonium saccharide.
2. Crystalline denatonium saccharide.
3. A composition for utilizing the bitter tasting property of denatonium saccharide at low concentrations comprising an effective amount of said compound and an inert and/or active material therewith.
4. A method of imparting a bitter tasting property to a substrate which comprises including into or onto said substrate an effective amount of denatonium saccharide.

* * * * *